(12) United States Patent
Kraemer et al.

(10) Patent No.: US 10,702,563 B2
(45) Date of Patent: Jul. 7, 2020

(54) METHODS OF MITIGATING THE NEGATIVE EFFECTS OF ENDURANCE EXERCISE

(71) Applicants: NU SCIENCE LABORATORIES, INC., Chestnut Hill, MA (US); William J. Kraemer, Columbus, OH (US)

(72) Inventors: William J. Kraemer, Columbus, OH (US); Mark G. Connell, Chestnut Hill, MA (US)

(73) Assignee: NU Science Laboratories, Inc., Chestnut Hill, MA (US)

(*) Notice: Subject to any disclaimer, the term of this patent is extended or adjusted under 35 U.S.C. 154(b) by 0 days.

(21) Appl. No.: 16/002,950

(22) Filed: Jun. 7, 2018

(65) Prior Publication Data
US 2018/0369305 A1   Dec. 27, 2018

Related U.S. Application Data

(63) Continuation of application No. 15/185,800, filed on Jun. 17, 2016, now Pat. No. 10,016,472, which is a continuation-in-part of application No. 14/406,752, filed as application No. PCT/US2013/045202 on Jun. 11, 2013, now abandoned.

(60) Provisional application No. 61/658,142, filed on Jun. 11, 2012, provisional application No. 62/180,831, filed on Jun. 17, 2015.

(51) Int. Cl.
| | |
|---|---|
| *A61K 49/00* | (2006.01) |
| *A61K 47/00* | (2006.01) |
| *A61K 31/34* | (2006.01) |
| *A61K 36/064* | (2006.01) |
| *A61K 31/7105* | (2006.01) |
| *A61K 31/711* | (2006.01) |

(52) U.S. Cl.
CPC .......... *A61K 36/064* (2013.01); *A61K 31/711* (2013.01); *A61K 31/7105* (2013.01)

(58) Field of Classification Search
CPC ........ A61K 31/70; A61K 36/06; A61K 38/00; A61K 39/00
USPC ......................................... 424/9.1, 439, 634
See application file for complete search history.

(56) References Cited

U.S. PATENT DOCUMENTS

| | | | |
|---|---|---|---|
| 10,016,472 B2 * | 7/2018 | Kraemer | A61K 36/064 |
| 10,271,570 B2 | 4/2019 | Connell | |
| 2005/0042328 A1 | 2/2005 | Nishiuchi et al. | |
| 2006/0239987 A1 | 10/2006 | Foster | |
| 2007/0190223 A1 | 8/2007 | Bordi, Jr. et al. | |
| 2013/0122139 A1 | 5/2013 | Savant et al. | |
| 2013/0129838 A1 | 5/2013 | Miller et al. | |
| 2014/0135257 A1 | 5/2014 | De Kort et al. | |
| 2015/0150898 A1 | 6/2015 | Connell | |

FOREIGN PATENT DOCUMENTS

| | | |
|---|---|---|
| WO | WO 2007/082267 | 7/2007 |
| WO | WO 2011/064373 | 6/2011 |
| WO | WO 2011/066175 | 6/2011 |
| WO | WO 2012/068431 | 5/2012 |

OTHER PUBLICATIONS

"10 Facts: How Many Carbs in a Banana," Thrombocyte, © 2016, 10 pages [retrieved May 16, 2016 from http://www.thrombocyte.com/how-many-carbs-in-a-banana/].
"Banana and Marmite on toast," The Lady Bites, Apr. 5, 2012, 3 pages [retrieved from: theladybites.co.uk/2012/04/banana-and-marmite-on-toast].
"The History of the Banana: Ancient Origins to the 1800s," University of California Santa Cruz, 3 pages [retrieved May 16, 2016 from: http://cwh.ucsc.edu/bananas/Site/Early%20History%20of%20the%20Banana.html].
"Marmite™ Nutrition," Sanitarium Health & Wellbeing, 2 pages [retrieved Jul. 28, 2017 from: marmite.co.nz/dig-deep/nutrition].
"Wily British Eat Bananas While Foes Slip on Peels," Los Angeles Times, Jan. 17, 1926, 1 page.
Biolo et al. "Physiologic hyperinsulinemia stimulates protein synthesis and enhances transport of selected amino acids in human skeletal muscle." The Journal of Clinical Investigation, Feb. 1995, vol. 95, No. 2, pp. 811-819.
Biolo et al. "Insulin action on muscle protein kinetics and amino acid transport during recovery after resistance exercise." Diabetes, May 1999, vol. 48, No. 5, pp. 949-957 (Abstract Only).
Boirie et al. "Differential Insulin Sensitivities of Glucose, Amino Acid, and Albumin Metabolism in Elderly Men and Women," The Journal of Clinical Endocrinology & Metabolism, Feb. 2001, vol. 86, No. 2, pp. 638-644.
Burke et al. "Original Research Effect of α-Lipoic Acid Combined With Creatine Monohydrate on Human Skeletal Muscle Creatine and Phosphagen Concentration," International Journal of Sport Nutrition and Exercise Metabolism, Sep. 2003, vol. 13, No. 3, pp. 1296-1301(Abstract only).
Kau et al. "Human nutrition, the gut microbiome and the immune system," Nature, Jun. 2011, vol. 474, pp. 327-336.
Kelly "The Effect of Total Work Performed During Acute Heavy Resistance Exercise on Circulating Lymphocytes in Untrained Men," University of Connecticut, Master's Theses, May 7, 2011, 51 pages.
Khan et al. "Insulin regulation of glucose uptake: a complex interplay of intracellular signalling pathways," Diabetologia, Nov. 2002, pp. 1475-1483.
Lozupone et al. "Diversity, stability and resilience of the human gut microbiota," Nature, Sep. 2012, vol. 489, pp. 220-230.
Odoom et al. "The regulation of total creatine content in a myoblast cell line," Molecular and Cellular Biochemistry, May 1996, vol. 158, No. 2, pp. 179-188 (Abstract Only).
Streeper et al. "Differential effects of lipoic acid stereoisomers on glucose metabolism in insulin-resistant skeletal muscle," American Journal of Physiology, Jul. 1997, vol. 273, No. 1, pp. E185-E191 (Abstract Only).

(Continued)

*Primary Examiner* — Rodney P Swartz
(74) *Attorney, Agent, or Firm* — Sheridan Ross P.C.

(57) ABSTRACT

Methods for inhibiting the negative metabolic and/or inflammatory impact of endurance exercise by administration of nucleotides is disclosed.

14 Claims, 7 Drawing Sheets

(56) References Cited

OTHER PUBLICATIONS

Wang et al. "Insulin Unmasks a COOH-Terminal Glut4 Epitope and Increases Glucose Transport across T-Tubules in Skeletal Muscle," Journal of Cell Biology, Oct. 1996, vol. 135, No. 2, pp. 415-430.
Ziegler et al. "Treatment of symptomatic diabetic polyneuropathy with the antioxidant alpha-lipoic acid: a 7-month multicenter randomized controlled trial (ALADIN III Study). ALADIN III Study Group. Alpha-Lipoic Acid in Diabetic Neuropathy." Diabetes Care, Aug. 1999, vol. 22, No. 8, pp. 1296-1301 (Abstract Only).
International Search Report and Written Opinion for International (PCT) Patent Application No. PCT/US13/45202, dated Nov. 12, 2013 14 pages.
International Preliminary Report on Patentability for International (PCT) Patent Application No. PCT/US2013/045202, dated Dec. 24, 2014 13 pages.
Official Action for U.S. Appl. No. 14/406,752, dated Jan. 25, 2016 11 pages.
Official Action for U.S. Appl. No. 14/406,752, dated Oct. 27, 2016 10 pages.
Official Action for U.S. Appl. No. 15/185,800, dated May 26, 2017 9 pages.
Official Action for U.S. Appl. No. 15/185,800, dated Nov. 30, 2017 8 pages.
Notice of Allowance for U.S. Appl. No. 15/185,800, dated Mar. 8, 2018 8 pages.
Official Action for U.S. Appl. No. 14/460,417, dated Jan. 15, 2016 11 pages Restriction Requirement.
Official Action for U.S. Appl. No. 14/460,417, dated Jun. 8, 2016 20 pages.
Official Action for U.S. Appl. No. 14/460,417, dated Aug. 7, 2017 15 pages.
Official Action for U.S. Appl. No. 14/460,417, dated Apr. 3, 2018 8 pages.
Notice of Allowance for U.S. Appl. No. 14/460,417, dated Jan. 25, 2019 8 pages.

* cited by examiner

METHODS OF MITIGATING THE NEGATIVE EFFECTS OF ENDURANCE EXERCISE

CROSS-REFERENCE TO RELATED APPLICATIONS

This application is a continuation of U.S. patent application Ser. No. 15/185,800, filed Jun. 17, 2016, now U.S. Pat. No. 10,016,472, issued Jul. 10, 2018; which is a continuation-in-part of U.S. patent application Ser. No. 14/406,752, now abandoned; which is a U.S. National Phase filing of PCT Application No. PCT/US13/45202, having an international filing date of Jun. 11, 2013, which designated the United States. PCT Application No. PCT/US13/45202 claims the benefit of priority under 35 U.S.C. § 119(e) to U.S. Provisional Patent Application No. 61/658,142, filed Jun. 11, 2012. This application also claims the benefit of priority under 35 U.S.C. § 119(e) to U.S. Provisional Patent Application No. 62/180,831, filed Jun. 17, 2015. The entire disclosures of U.S. patent application Ser. No. 15/185,800, PCT/US13/45202 and each U.S. Provisional Patent Application Nos. 61/658,142 and 62/180,831 are incorporated herein by reference.

FIELD OF THE INVENTION

The present invention is directed to nutritional products, including solid and liquid products, useful for athletes during recovery from exercise and methods of use of the same.

BACKGROUND OF THE INVENTION

Nutritional products for athletes typically address a single need of the athlete. Most products focus on supply of either energy (carbohydrate and electrolyte based products) or protein. When consumed within an hour after exercise, carbohydrates help to quickly rebuild energy stores through restoring muscle and liver glycogen. Protein and amino acid based products can help speed absorption of carbohydrates and provide building blocks to repair muscles.

None of these types of products can address the initiation of tissue recovery, which is mediated by the immune system. In addition, there is a frequently noted correlation between prolonged heavy exercise and upper respiratory tract infection (URTI). While the causal pathways are not certain, it is recognized that exercise has multiple effects on the immune system which might explain these observations.

It is widely accepted that both acute and chronic exercise alter the number and function of circulating cells of the innate immune system (e.g., neutrophils, monocytes and natural killer (NK) cells). Similarly, it is agreed that a lymphocytosis is observed during and immediately after exercise, proportional to exercise intensity and duration, with the number of cells (T cells and to a lesser extent B cells) falling below pre-exercise levels during the early stages of recovery, before returning to resting values normally within 24 hours. Finally, a consensus exists that reduced levels of secretory immunoglobulin A (SIgA) are associated with increased risk for URTI during heavy training as the production of SIgA is the major effector function of the mucosal immune system providing the 'first line of defense' against pathogens. Thus, there is an ongoing need to manage and reduce the negative effects of exercise on the immune system to keep athletes healthy and performing at their highest levels.

Further, independent of immune system effects, there is a need to improve performance levels of athletes for athletes of all calibers.

SUMMARY OF THE INVENTION

One embodiment of the present invention is a method to inhibit resistance exercise-induced production of cortisol which includes administering a composition comprising a nucleotide component to an athlete engaging in resistance exercise.

A further embodiment of the present invention is a method to inhibit resistance exercise-induced production of myeloperoxidase which includes administering a composition comprising a nucleotide component to an athlete engaging in resistance exercise.

A further embodiment of the present invention is a method to inhibit resistance exercise-induced production of creatine kinase which includes administering a composition comprising a nucleotide component to an athlete engaging in resistance exercise.

A further embodiment of the present invention is a method to inhibit resistance exercise-induced impairment of isometric force generation which includes administering a composition comprising a nucleotide component to an athlete engaging in resistance exercise.

In the various methods of the invention, the nucleotide-containing composition can be prior to and/or after the resistance exercise. In one embodiment, dosing can include administration of two nucleotide-containing capsules (containing between about 250 mg and about 300 mg of dietary nucleotides) in the morning and two after exercise, such as on a daily basis. In other embodiments, the nucleotide component is administered in an amount between about 10 mg and about 1000 mg on a daily basis, between about 100 mg and about 900 mg on a daily basis or between about 400 mg and about 800 mg on a daily basis.

In the various methods of the invention, the nucleotide-containing composition can include RNA and DNA, an extract of a yeast, or an extract of a yeast selected from the group consisting of *Saccharomyces cerevisiae* and *Candida utilis*.

In the various methods of the invention, the resistance exercise includes acute heavy resistance exercise and can include weightlifting, sprinting, field events, football, martial arts, wrestling, or boxing.

DETAILED DESCRIPTION

Figure 1:
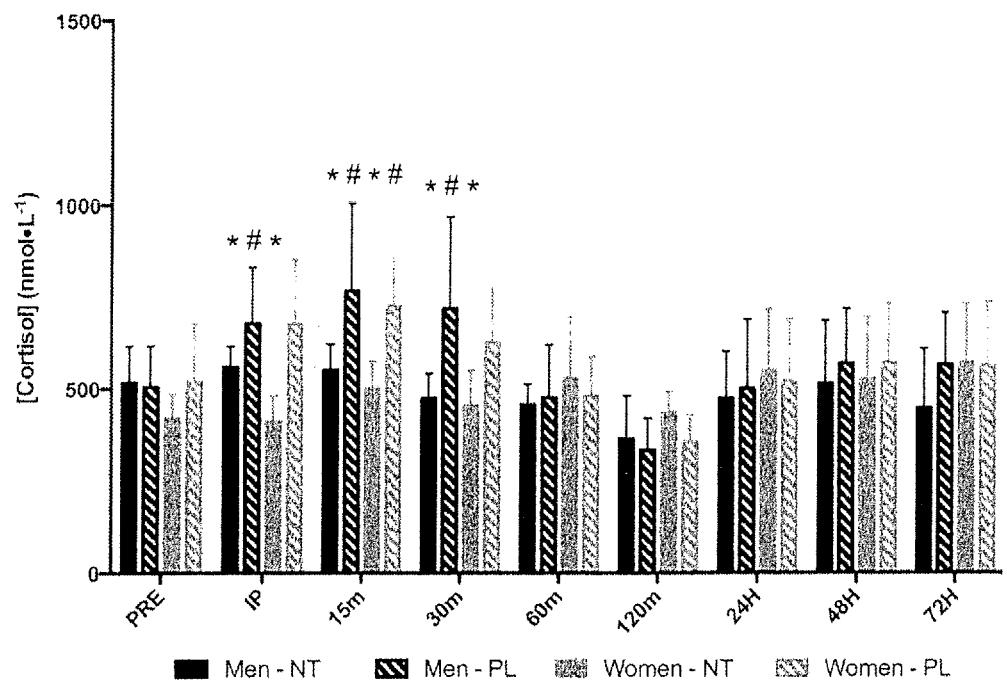
FIG. 1 illustrates the cortisol response to resistance exercise.

Various embodiments of the present invention include products that comprise a nucleotide component and one or more additional components, as well as related methods of administration, such as for treating athletes. Such additional components can include, for example, a carbohydrate component, a protein component and/or a polyunsaturated fatty acid (PUFA), among other components described herein.

One embodiment of the present invention is a sports nutritional product that includes a nucleotide component, a carbohydrate component, a protein component, and a polyunsaturated fatty acid (PUFA) component. Such products are primarily intended for use by athletes and individuals involved in athletic training. Therefore, such individuals are adults and teenagers who eat a diet of solid food. Such individuals do not include infants or babies, and therefore, sports nutritional products of the present invention do not include infant formulae or other types of food intended to be fed to infants or babies. Accordingly, sports nutritional products of the present invention do not include ingredients that are unique to infant formulae or other types of food intended to be fed to infants or babies. For example, such ingredients in infant formulae or other types of food intended to be fed to infants or babies but not in sports nutritional products of the present invention can be arachidonic acid. Sports nutritional products of the present invention including nucleotide, carbohydrate, protein and PUFA components provide a unique combination of nutritional elements for an athlete.

There are numerous existing products that provide carbohydrates as well as products that provide protein. Many offer them in various combinations. Carbohydrates provide the raw material to quickly rebuild the body's readily available energy stores (i.e., glycogen stored in both muscles and the liver), particularly if consumed within a short time period after exercise when the hormonal environment in the body allows rapid conversion of glucose to glycogen. Protein (particularly those high in branched chain amino acids) provides raw material for rebuilding muscles. However, neither of these components, alone or in combination, provides the immune system benefits supported by the availability of nucleotides in compositions of the present invention.

Nucleotide

The term nucleotide refers to a compound that has a nitrogenous base, a pentose sugar and one or more phosphate groups. The nitrogenous base is either a purine or a pyrimidine. Pyrimidine bases are six-membered rings, and include uracil (U), cytosine (C) and thymine (T). Purine bases have a second five-membered ring, and include adenine (A), guanine (G), hypoxanthine and xanthine. A purine or pyrimidine based linked to a pentose molecule constitutes a nucleoside. A nucleotide is a phosphate ester of a nucleoside, and may occur in the monophosphate, diphosphate or triphosphate form. The pentose is either ribose or deoxyribose; the ribonucleotide and deoxynucleotide serve as the monomeric units of RNA and DNA, respectively. RNA and DNA are linear polymers consisting of four different nucleotides linked together by 5',3' phosphodiester bonds. Nucleotides of the present invention include any compound or composition that is a source of nucleotides, and thus, can include individual nucleotides, dinucleotides, trinucleotides and oligonucleotides (comprising up to about 50 bases), as well as longer polynucleotides.

Nucleotide components of the present invention can comprise extracts of yeast, such as *Saccharomyces cerevisiae* (brewer's yeast) or *Candida utilis* (formerly *Torulopsis utilis* or *Torula utilis*) (produced from wood sugars as a by-product of paper production).

Suitable nucleotide sources for the present invention include commercially available ones such as nuBound Recovery Supplement (Nu Science Laboratories, Inc., Chestnut Hill, Mass.). Other commercially available products include Life Extension RNA Capsules; Bluebonnet Kosher Nucleotide Complex 300; Good N Natural RNA/DNA; VitaminLife DNA/RNA; and Country Life RNA/DNA.

Nucleotide components of the present invention can be present in products such that the amount of nucleotide delivered per serving is between about 10 mg and about 1000 mg, between about 100 mg and about 900 mg, or between about 400 mg and about 800 mg. In other embodiments, the nucleotide component per serving can be present in ranges having a lower end of the range of about 10 mg, about 20 mg, about 30 mg, about 40 mg, about 50 mg, about 60 mg, about 70 mg, about 80 mg, about 90 mg, about 100 mg, about 200 mg, about 300 mg, or about 400 mg and having a higher end of the range of about 1000 mg, about 900 mg, about 800 mg, about 700 mg, about 600 mg, about 500 mg, about 400 mg, about 300 mg, about 280 mg, about 260 mg, about 240 mg, about 220 mg, about 200 mg, about 190 mg, about 180 mg, about 170 mg, about 160 mg, about 150 mg, about 140 mg, about 130 mg, about 120 mg, about 110 mg, or about 100 mg. It should be recognized that the foregoing amounts are per serving and that a serving can be prepared in different product forms depending on how much of a nucleotide component is included in a product. For example, a serving may be one-half or an entire sports drink, an entire sports bar, two cookies or 4 capsules.

Without intending to be bound by theory, in various products of the present invention, the nucleotide component can play one or more of a variety of functions. Nucleotides are a key component in several major processes within the body and play key roles in many biological processes. The requirements for nucleotides may increase when recovering from major tissue injury, systemic infection or possible when liver function in suppressed. A nucleotide rich diet has been shown to result in improved immune function, improved growth and resistance to infection. Nucleotides can offset the negative hormonal response associated with metabolic or inflammatory insult, such as by demanding endurance exercise (i.e., exercise using slow twitch muscle fibers and aerobic energy pathways) and/or demanding strength and power exercise (i.e., exercise using fast twitch muscle fibers and anaerobic energy pathways).

Additional components of products of the present invention, include carbohydrates, proteins (including protein derivatives, such as hydrolysates and amino acids), polyunsaturated fatty acids (particularly, including ω-3 polyunsaturated fatty acids), antioxidants (e.g., vitamins C and E, beta-carotene, N-acetylcysteine and butylated hydroxyanisole), glutamine, *ginseng, echinacea*, bovine colostrum, immunoferon, zinc, plant sterols, and non-steroidal anti-inflammatory compounds.

Carbohydrates

As used herein, "carbohydrate" refers to a source of carbohydrates such as, but not limited to, monosaccharides, disaccharides, oligosaccharides, polysaccharides or derivatives thereof. Such carbohydrates can include without limitation glucose, sucrose, fructose, dextrose and lactose. Particularly preferred sugars include glucose, dextrose, lactose and other non-fructose-based saccharides. Another preferred carbohydrate is a large glucose polymer having a molecular weight between 500,000 and 700,000 which is known commercially as SuperStarch. This product has a low osmolality with a slow "time-released" glucose profile and low insulin impact to avoid the spike and crash phenomena and extend maintenance of blood glucose. This product is available from the UCAN Company of Woodbridge, Conn.

Carbohydrate ingestion is known to stimulate the secretion of insulin which in turn facilitates the uptake of glucose into skeletal muscle via glucose transporter 4 (GLUT4) translocation. Glucose is then converted to and stored as glycogen and triglycerides. Concomitant with this, insulin inhibits the release and synthesis of glucose. Moreover, insulin also plays an important role in protein metabolism where it inhibits the breakdown of protein or proteolysis. Furthermore, insulin promotes the uptake of amino acids into muscle and stimulates protein synthesis, particularly following exercise. Insulin has also been shown to stimulate creatine uptake by muscle cells. Alpha Lipoic Acid has been shown to have insulin-like properties, which further aid in the retention of Creatine. Via the combination of creatine with alpha lipoic acid and a small amount of carbohydrate, creatine retention as compared to Creatine and carbohydrate alone is significantly improved. Therefore, it is advantageous that, for the purposes of creatine retention, the actions of insulin be enhanced. Furthermore, it may be advantageous to increase the activity and availability of creatine in skeletal muscle. Carbohydrates have been shown to attenuate increases in plasma cytokines and stress hormones during demanding endurance exercise.

Some embodiments of the present invention include liquid drink products. While rehydration can be a major reason to consume drink products, the ability to furnish rapidly-absorbed carbohydrates can be very important. Hundreds of research studies over the past 3 decades have proven that ingesting carbohydrates during prolonged strenuous exercise enhances performance compared to plain water. Thus, drink products can serve two roles: (a) rehydration and (b) fuel for exercising muscles. Research shows that, when the carbohydrate concentration in a beverage increases above 8%, gastric emptying slows. This is a critical factor in the development of drink products since strenuous exercise by itself can impair gastric emptying: as exercise intensity increases, the rate of gastric emptying decreases. Thus, if one drinks beverages with a carbohydrate concentration greater than 8% while running, not only does this impair the delivery of fuel to exercising muscles, you may be more likely to develop gastrointestinal intolerance (stomach cramps, vomiting).

According to some research, the optimum concentration of carbohydrate in a drink product is 6-8%. This concentration can also be expressed as:

6-8 grams per 100 ml
14.2-18.9 grams per 8 oz.
21.3-28.4 grams per 12 oz.

Further, it has been shown that absorption and oxidation of carbohydrates during strenuous exercise is optimized if carbohydrates are supplied in a mixture of several types, as opposed to a single carbohydrate source. For example, carbohydrates can come from a mixture of sucrose syrup and glucose-fructose syrup.

More generally in products of the present invention, the amount of carbohydrates can be present in products such that the amount of carbohydrate delivered per serving is between about 2 gm and about 40 gm, between about 5 gm and about 30 gm, or between about 10 gm and about 20 gm. In other embodiments, the carbohydrate component per serving can be present in ranges having a lower end of the range of about 2 gm, about 3 gm, about 4 gm, about 5 gm, about 6 gm, about 7 gm, about 8 gm, about 9 gm, about 10 gm and having a higher end of the range of about 40 gm, about 38 gm, about 36 gm, about 34 gm, about 32 gm, about 30 gm, about 28 gm, about 26 gm, about 24 gm, about 20 gm, about 18 gm, about 16 gm, about 14 gm, about 12 gm, or about 10 gm.

Polyunsaturated Fatty Acids (PUFA)

In some embodiments of the present invention, nutrition products include a PUFA, which can be a PUFA having a chain length of at least 18 carbons or at least about 20 carbons. PUFAs useful in the present invention can be ω-3 (final double bond three positions from the methyl end of the fatty acid). In some embodiments, the PUFA has at least three double bonds. Examples of PUFAs are docosahexaenoic acid C22:6(n-3) (DHA), omega-3 docosapentaenoic acid C22:5(n-3) (DPA), eicosapentaenoic acid C20:5(n-3) (EPA), stearidonic acid, α-linolenic acid (ALA) or mixtures thereof. The PUFAs can be in any of the common forms found in natural lipids including but not limited to triacylglycerols, diacylglycerols, monoacylglycerols, phospholipids, free fatty acids, esterified fatty acids, or in natural or synthetic derivative forms of these fatty acids (e.g. calcium salts of fatty acids, ethyl esters, etc.). Reference to a PUFA-containing composition, as used in the present invention, can refer to either a composition comprising only a single PUFA such as DHA or a composition comprising a mixture of two or more PUFAs such as DHA and EPA, DHA and DPA, EPA and DPA or DHA, DPA, and EPA.

In some embodiments, the PUFA-containing composition is selected from the group of a microbial oil, a plant seed oil, and an aquatic animal (e.g., fish) oil. More generally in products of the present invention, the amount of PUFA can be present in products such that the amount of PUFA delivered per serving is between about 50 mg and about 4000 mg, between about 100 mg and about 3000 mg, between about 150 mg and about 2000 mg, or between about 200 mg and about 1000 mg. In other embodiments, the PUFA component per serving can be present in ranges having a lower end of the range of about 50 mg, about 60 mg, about 70 mg, about 80 mg, about 90 mg, about 100 mg, about 125 mg, about 150 mg, about 175 mg, about 200 mg, about 250 mg, about 300 mg, about 350 mg, about 400 mg, about 450 mg, about 500 mg, about 600 mg, about 700 mg, about 800 mg, about 900 mg or about 1000 mg and having a higher end of the range of about 4000 mg, about 3500 mg, about 3000 mg, about 2500 mg, about 2000 mg, about 1500 mg, about 1400 mg, about 1300 mg, about 1200 mg, about 1100 mg, about 1000 mg, about 900 mg, about 800 mg, about 700 mg, about 600 mg, or about 500 mg.

PUFAs of compositions of the present invention can provide an important anti-inflammatory activity to inhibit inflammation occurring as a result of athletic endeavors. It has been recognized that prolonged aerobic (or endurance) exercise as well as strength or resistance exercise provide inflammatory stimuli occurring as a result of muscle damage from the exercise. It is thought that the primary functions of exercise-induced leukocytes are attack and breakdown of debris, clearance of cellular debris and regeneration of muscle cells. The immune response to endurance and resistance exercise serve the same purpose and have similarities in leukocytotic patterns, resistance exercise-induced leukocytosis is less pronounced with the exception that lymphocyte response seems to be increased dramatically immediately post-resistance exercise. Kelly, Neil A. Jr., "The Effect of Total Work Performed During Acute Heavy Resistance Exercise on Circulating Lymphocytes in Untrained Men" (2011). *Master's Theses*. Paper 48.

Proteins

Sports nutrition products that contain protein components can be more efficient at increasing both muscle glycogen and the muscle protein after strenuous exercise. Several studies show that exercise performance is better in athletes who consume carbohydrate and protein-containing beverages compared to athletes who received the carbohydrate-only type. Further, muscle injury and/or soreness may be less when protein is ingested after strenuous exercise. Several studies show that CPK levels (a marker for muscle injury) are lower if a carbohydrate and protein-containing product is consumed immediately following exercise. Marine recruits who received protein supplementation immediately postexercise had less muscle soreness.

Protein for products of the present invention can be derived from a variety of sources. For example, soy protein, whey protein or casein protein can be used. Protein sources can be hydrolyzed to varying degrees, including smaller protein molecules, peptides (including dipeptides, tripeptides and oligopeptides) and single amino acids. Preferred sources of protein are sources that are relatively high in the content of branched chain amino acids (leucine, isoleucine and valine), such as whey protein.

Preferred single amino acid sources include the amino acid arginine. In embodiments including arginine, it is particularly preferred to include ω-3 PUFA because of their anti-inflammatory properties.

Protein components of the present invention are present in products such that the amount of protein delivered per serving is between about 10 gm and about 100 gm, between about 20 gm and about 80 gm, or between about 30 gm and about 60 gm. In other embodiments, the nucleotide component per serving can be present in ranges having a lower end of the range of about 10 gm, about 20 gm, about 30 gm, about 40 gm, or about 50 gm, and having a higher end of the range of about 100 gm, about 90 gm, about 80 gm, about 70 gm, about 60 gm, or about 50 gm.

Antioxidants

Various embodiments of the present invention include antioxidants, including but not limited to vitamin C, vitamin E, beta-carotene, lutein, lycopene, Vitamin B2, CoEnzyme Q10, cysteine, N-acetylcysteine, butylated hydroxyanisole, manganese, copper, zinc and selenium. Antioxidants can be used in products of the present invention in amounts known to those of skill in the art.

Non-Steroidal Anti-Inflammatory (NSAID)

Various embodiments of the present invention include the use of non-steroidal anti-inflammatory (NSAID) compounds. Such components can offset the negative hormonal response associated with metabolic or inflammatory insult, such as by demanding endurance exercise. NSAIDs useful in the present invention can include without limitation, salicylates (aspirin (acetylsalicylic acid), diflunisal, salsalate); propionic acid derivatives (ibuprofen, Naproxen, Fenoprofen, Ketoprofen, Flurbiprofen, Oxaprozin, Loxoprofen); acetic acid derivatives; enolic acid (Oxicam) derivatives; fenamic acid derivatives (Fenamates); selective COX-2 inhibitors (Coxibs); and sulphonanilides.

Products of the present invention can be in various forms. For example, the products can be either liquid products that are drinkable or they can be solid forms that can be eaten.

Various embodiments of the present invention include drinkable liquids including one or more of the active components described above. Drinkable liquids include clear liquid products as well as shake-like products. Drinkable liquids include a fluid, typically water, and other components. In addition to other components described herein, drinkable liquids can include electrolytes, such as sodium, potassium and other known electrolytes. The optimum concentration of sodium in a sports rehydration drink is 20-40 mmol/liter.

In drinkable liquids that include carbohydrates, such carbohydrates can include, for example, fructose, glucose, maltodextrin, sucrose or combinations thereof. Such drinkable liquids can include carbohydrates in a concentration of about 2.0-8.75% with an osmolality of less than about 400 mOsm.

Solid product forms of the sports nutritional products can include, without limitation bars, cookies, gels, powders, capsules.

A preferred embodiment of the present invention is a composition comprising a nucleotide component, a carbohydrate component, a protein component and PUFA component. This composition is particularly useful for aiding in the recovery of athletes after a workout. The functions of the various components are described in detail above. The composition can be formulated in a number of different product types. Preferred formulations include a drinkable liquid, for example, as a shake-type drink. Alternatively, this composition can be formulated as a dry powder that is rehydrated with water to form a drinkable product. Other embodiments include forming the composition in an edible form such as a bar, cookie or gel.

Products of the present invention can include other components useful for preparing the products in conventional forms such as shakes, drinks, bars, etc. For example, such other components can include flavors, sweeteners, colors, binders, texture modifiers and the like.

Another embodiment of the present invention is a method to inhibit exercise-induced impairment of immune function by administering a composition to an athlete engaging in exercise, wherein the composition includes a nucleotide component. As discussed above, there is a correlation between exercise and reduced immune function. The present invention, involving the administration of nucleotide-containing compositions to athletes and those involved in athletic pursuits, can reduce or inhibit the suppression of immune function associated with exercise in the absence of administration of compositions of the present invention. As such, the present invention can improve the health of athletes. This method is particularly useful for athletes, who in addition to the risk of exercise-induced impairment of immune function, otherwise have or at risk of having impaired immune function. Such additional risk factors can include, without limitation, level of stress, poor nutrition, and lack of sufficient sleep.

For example, immune function can be measured in a variety of ways known to those skilled in the art. For examples, body samples, such as blood samples, from an athlete can be analyzed for blood cell counts, such as by conducting a complete blood count (CBC) and/or looking at one or more markers. For example, samples can be evaluated for hormones or markers thereof (e.g., catecholamines, cortisol or lactate, wherein for example, reduced levels of cortisol after exercise indicate improved function), nucleotide markers (e.g., glutamine, glutamate, or uric acid wherein increased levels indicate use of nucleotides by the body), or markers of oxidative stress (e.g., malondialdehyde (MDA) or myeloperoxidase (MPO) wherein reduced levels indicate improved function). Also, samples can be evaluated for levels of SIgA and/or natural killer (NK) cells, wherein for example, increased levels of either or both indicates improved function.

A further method of the present invention is a method to improve exercise performance by administering a composition to an athlete engaging in exercise, wherein the composition comprises a nucleotide component. There is always a need for athletes, whether or not competitive athletes, to improve their performance in their selected athletic pursuit. The present invention, involving the administration of nucleotide-containing compositions to athletes and those involved in athletic pursuits, can improve the performance of the athlete in their sport or athletic endeavor as compared to performance of the athlete in the absence of administration of compositions of the present invention.

Quantification of improved performance will of course depend on the nature of the athletic endeavor involved. For example, in the instance of a weightlifter, improved performance can be easily objectively measured for example, by the ability to perform a weightlifting exercise at either greater weights or higher repetitions. Similarly, in the case of a runner, improved performance can be measured by completing a fixed distance in a shorter time period.

A further embodiment of the present invention, as illustrated in the Example, is a method to inhibit resistance exercise-induced production of cortisol which includes administering a composition comprising a nucleotide component to an athlete engaging in resistance exercise. Suitable nucleotide-containing compositions are described herein. Suitable dosing can include as described in the Example, administration of two nucleotide-containing capsules (containing between about 250 mg and about 300 mg of dietary nucleotides) in the morning and two after exercise.

A further embodiment of the present invention, as illustrated in the Example, is a method to inhibit resistance exercise-induced production of myeloperoxidase which includes administering a composition comprising a nucleotide component to an athlete engaging in resistance exercise. Suitable nucleotide-containing compositions are described herein. Suitable dosing can include as described in the Example, administration of two nucleotide-containing capsules (containing between about 250 mg and about 300 mg of dietary nucleotides) in the morning and two after exercise.

A further embodiment of the present invention, as illustrated in the Example, is a method to inhibit resistance exercise-induced production of creatine kinase which includes administering a composition comprising a nucleotide component to an athlete engaging in resistance exercise. Suitable nucleotide-containing compositions are described herein. Suitable dosing can include as described in the Example, administration of two nucleotide-containing capsules (containing between about 250 mg and about 300 mg of dietary nucleotides) in the morning and two after exercise.

A further embodiment of the present invention, as illustrated in the Example, is a method to inhibit resistance exercise-induced impairment of isometric force generation which includes administering a composition comprising a nucleotide component to an athlete engaging in resistance exercise. Suitable nucleotide-containing compositions are described herein. Suitable dosing can include as described in the Example, administration of two nucleotide-containing capsules (containing between about 250 mg and about 300 mg of dietary nucleotides) in the morning and two after exercise.

In preferred embodiments of methods of the invention, such individuals are athletes that have physically exerted themselves through exercise and/or are otherwise susceptible to muscle injury, inflammation and other conditions associated with physical exertion. Such athletes are typically human athletes but can also be non-human athletes such as racehorses and racing dogs. The methods include administering a nutritional product to the athlete before and/or after the athlete has physically exerted himself/herself. The nutritional product includes a nucleotide component and optionally, can include a component selected from a carbohydrate component, a protein component, a PUFA component and combinations thereof. The various embodiments of the product components are described above.

Athletes for whom the present invention is useful can be male or female and in various embodiments, can be 20 years or older, can be 30 years or older, can be 40 years or older, can be 50 years or older, can be 60 years or older. Such athletes can be characterized, for example, as endurance athletes or as strength athletes, although a given individual can of course be in both categories. An endurance athlete, for example, typically participates in sports, exercise or similar endeavors involving the use and development of cardiovascular capability, such as long distance running, cycling, swimming, hiking, triathlon, softball, baseball, soccer, basketball, hockey, football, rugby, tennis, lacrosse and so forth. Such endurance endeavors typically involve exercise using slow twitch muscle fibers and aerobic energy pathways. A strength athlete, for example, typically participates in sports, exercise or similar endeavors involving the use and development of strength capability, such as weightlifting, sprinting, field events (e.g., shot put), football, martial arts, wrestling, boxing, etc. Such strength endeavors typically involve exercise using fast twitch muscle fibers and anaerobic energy pathways. Other relevant sports include archery, basketball, badminton, volleyball, canoeing, diving, fencing, gymnastics, handball, hockey, rowing, sailing, softball, cricket, field hockey, skateboarding, snowboarding, surfing, bowling, golf, rock-climbing, mountaineering, racquetball, squash, skiing, and skating.

Sports exist on a continuum that runs from pure strength-power sports that are short duration/high intensity (e.g., weightlifting, shotput, hammer throw, etc.) to those that are pure endurance sports that are long duration/low intensity (e.g., marathon running, ultra-marathons, ironman triathlons, etc.). On the strength-power end of the spectrum athletes are using predominantly fast twitch muscle fibers, which are best trained with resistance exercise, while on the endurance end of the spectrum athletes are using predominantly slow twitch muscle fibers, which are best trained with endurance exercise. Anaerobic metabolism predominates in strength-power events, while aerobic metabolism predominates in endurance sports.

The majority of sports exist along the middle of this spectrum and require bursts of effort at times followed by opportunities for recovery. As such, athletes will typically combine resistance and endurance exercises in their training to produce a balance of strength and endurance. For example, a sprinter would focus on short repeats and incorporate a relatively large component of strength (resistance) training, but would still include some longer runs in their training program. On the other hand a marathon runner would train with runs that might last several hours, including a certain number of long repeats and would minimize resistance training.

Products of the present invention can be administered before and/or after an individual has engaged in a particular form of exercise and physically exerted himself or herself. Such physical exertion is typically the participation in one or more sports described above, such as running, cycling or weightlifting. One method of measuring physical exertion is by the heart rate of the individual. For example, the product can be administered after an individual has achieved an elevated heart rate, and more particularly, achieved an elevated heart rate for at least about 15 minutes, at least about 30 minutes, at least about 45 minutes, at least about 1 hour, at least about 1.5 hours, at least about 2 hours, at least about 2.5 hours, or at least about 3 hours. In this context, an elevated heart rate can be an average heart rate during the physical exertion of at least about 80 beats per minute (BPM), at least about 90 BPM, at least about 100 BPM, at least about 110 BPM, at least about 120 BPM, at least about 130 BPM, at least about 140 BPM or at least about 150 BPM.

More particularly, the product can be administered either before, during and/or after the physical exertion. For example, the product can be administered on a chronic basis, such as daily, every other day, every third day, etc. for a period of time of at least about 1 week, at least about 2 weeks, at least about 3 weeks, at least about 4 weeks, at least about 2 months, at least about 3 months at least about 6 months or longer.

Example

This example investigates the effects of nucleotide supplementation on the acute cortisol and immune responses to heavy resistance exercise and its effects on recovery. A double-blinded, crossover, mixed methods design with 10 men and 10 women was used.

Supplement Protocol

The nuBound (Nu Science Laboratories, Inc., Boston, Mass., USA) supplement contains dietary nucleotides, which are extracted from yeast (*Saccharomyces cerevisiae*). During the supplement treatment cycle, subjects took 4 capsules of nuBound daily, 2 upon waking, and 2 after exercise. Each dose of 2 capsules (1,000 mg) contained 278 mg of dietary nucleotides, 375 mg amino acids (L-glutamine, L-methionine, and L-lysine), riboflavin (4.5 mg), folate (400 mg), biotin (188 mg), and pantothenic acid (12 mg). Other ingredients included fructooligosaccharides (chicory root), inositol, and sodium citrate.

During the placebo cycle, subjects followed an identical dosing schedule. The placebo capsules were the same size, shape, and color of the nucleotide supplement but contained lactose and magnesium stearate. During the first treatment cycle, subjects recorded their daily dietary intake on a diet log. The log was then used to help subjects replicate their diet during the second treatment cycle. Subjects also replicated their physical activity during each cycle.

Acute Heavy Resistance Exercise Protocol

The AHREP consisted of 6 sets of 10 repetitions of back squats to parallel on a Smith machine, allowing only vertical translation of the bar. The starting weight was approximately 75% of the one rep maximum, as previously determined. If a subject was unable to complete all 10 repetitions, the weight was reduced at the discretion of the testers, and the remaining repetitions were completed. The weight was reduced to allow for completion of the required repetitions, with the goal of achieving the highest possible load volume. After the first and second sets, 2 minutes of rest were given; 3 minutes were given after each of the remaining sets as pilot testing indicated the additional rest allowed subjects to complete the AHREP with a higher load.

Performance Measures

Peak force was obtained during a maximal isometric squat, and peak power was obtained during a series of 3 maximal effort countermovement jumps. The maximal isometric squat was performed on a Smith machine, with force production measured and analyzed using a force plate (Fitness Technology 400 series performance force plate, Australia) and Ballistic Measurement System software (Software Version 2009.0.0). The height of the Smith machine bar was adjusted so that subjects were positioned with an approximate 135° knee joint angle. Subjects were instructed to push into the bar as if they were performing a squat, gradually increasing force until they reached maximal effort, holding the maximal effort, and then a slow reduction of force to resting levels (a trapezoidal force development curve). The total length of time for the isometric squat test was 10 seconds. Countermovement jumps were also performed on a force plate. Subjects kept their hands on their hips and performed 3 consecutive maximal-effort countermovement jumps.

Blood Collection

On the day of the AHREP, blood was collected at PRE (before protocol), IP (immediately following protocol), and 15, 30, 60, and 120 minutes after AHREP through an indwelling cannula kept patent with sterile saline. Before each blood draw, 3 ml of fluid was extracted and discarded. Single blood draws were taken at 24, 48, and 72 hours after AHREP. Whole blood was collected and placed in serum tubes or plasma tubes. The samples were then centrifuged, aliquoted, and stored at 80° C. until subsequent analyses.

Biochemical Analyses

The creatine kinase-SL assay (SEKISUI, Charlottetown, Canada) was performed in duplicate using serum samples. A Thermo Scientific BioMate 3 Spectrophotometer (Pittsburgh, Pa., USA) was used to read the assays at a wavelength of 340 nm. The coefficient of variation (CV) was 4.2%. Lactate was measured in EDTA-plasma samples using a liquid lactate reagent (Pointe Scientific, Canton, Mich., USA) and assayed according to Gutmann et al. and Noll et al. Serum uric acid was measured using uric acid reagents purchased from Pointe Scientific (Canton, Mich., USA) and performed according to the manufacturer's instructions. Serum cortisol was measured using an enzyme-linked immunosorbent assay (ELISA) (CALBiotech, Spring Valley, Calif., USA), with a sensitivity of 11.1 nmol $L^{-1}$. Myeloperoxidase (MPO) was measured in EDTA-plasma samples using an ELISA (ALPCO, NH, USA) with a sensitivity of 1.08 ng $mL^{-1}$. Lactate, uric acid, cortisol, and MPO were analyzed in duplicate on a VersaMax tunable microplate reader (Molecular Devices, Sunnyvale, Calif., USA) at the appropriate wavelength for the given assay. Intra- and inter-assay CVs for lactate, uric acid, cortisol and MPO were below 3.9%, 4.7%, 7.2%, and 6.3%, respectively.

Whole blood was analyzed for absolute neutrophil, lymphocyte, monocyte, eosinophil, and basophil counts by Quest Diagnostics (Madison, N.J., USA) using an automated hematology analyzer.

Statistical Analyses

Data are presented as mean±SD. Normality and homogeneity of variance were confirmed for the selected dependent variables. Data were analyzed using 1 between (sex) by 2 within (treatment and time point) mixed methods analyses of variance. When significant differences were detected, Fisher's least significant difference post hoc analyses were performed to make pairwise comparisons. Statistical significance was set at $p \leq 0.05$.

Results

The primary finding of this investigation was that nucleotide supplementation significantly altered resistance exercise-induced changes in cortisol, myeloperoxidase (MPO), creatine kinase (CK) concentrations, and isometric force production. As expected, the stress of the AHREP perturbed all variables measured. Sex differences were observed in terms of lactate, MPO, CK, isometric force, and countermovement jump power.

The AHREP induced significant acute increases in cortisol values in male and female placebo groups, which returned to baseline by 60 and 30 minutes after AHREP, respectively. In both sexes, nucleotide supplementation resulted in significantly lower cortisol values at IP and after 15 and 30 minutes when compared with the corresponding time points under placebo. No sex-specific differences were observed. Cortisol values are presented in FIG. 1.

Figure 2:
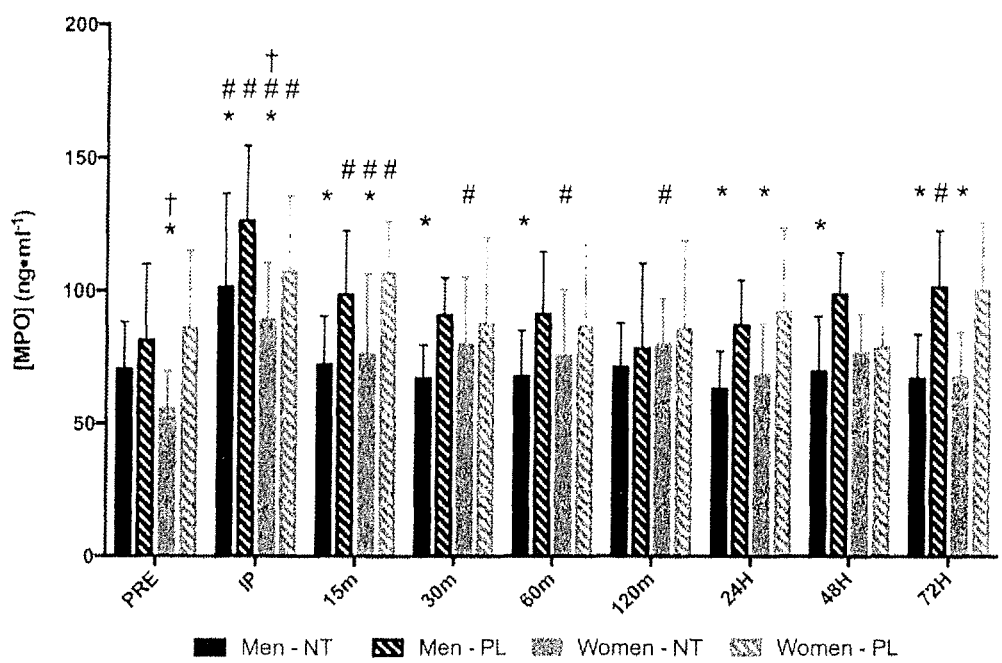
FIG. 2 illustrates the myeloperoxidase response to resistance exercise.

After the AHREP, MPO increases were observed in both sexes under both treatment conditions. Additionally, men demonstrated elevated MPO levels at 72 hours after AHREP under the placebo treatment only. Acutely, nucleotide supplementation resulted in significantly reduced MPO levels after the AHREP and during recovery time points in both men and women. Women demonstrated reduced MPO values at rest after nucleotide supplementation. The MPO values are presented in FIG. 2.

Figure 3:
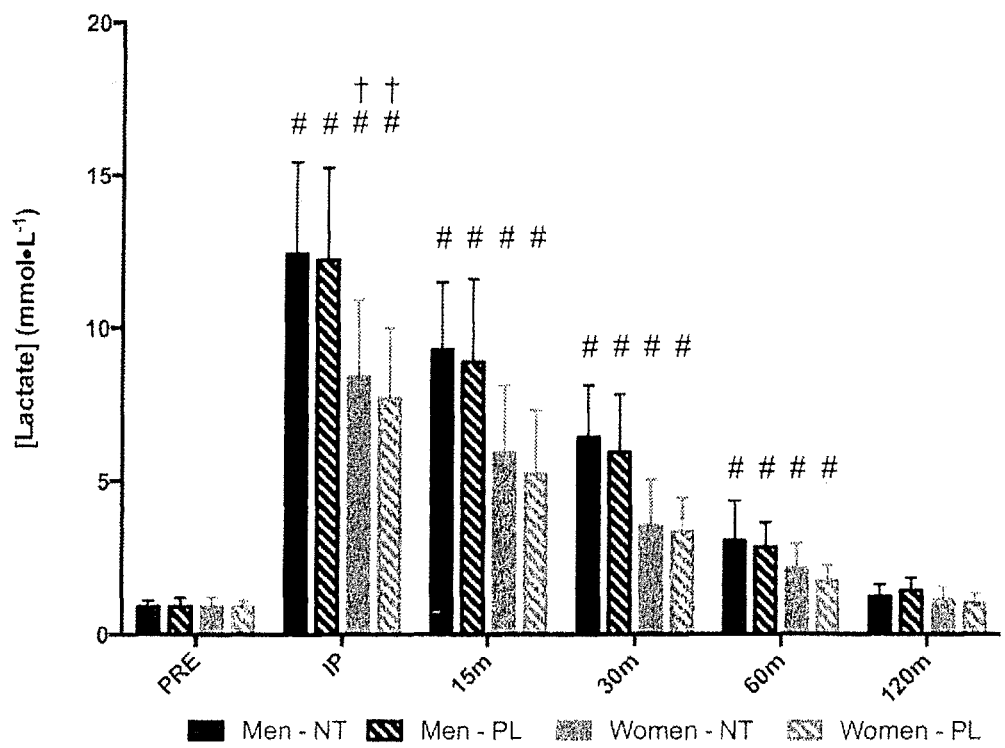
FIG. 3 illustrates the lactate response to resistance exercise.

Acute elevations in lactate were observed after the AHREP under both treatment conditions in both sexes. All groups demonstrated elevations at IP and after 15, 30, and 60 minutes, but returned to baseline values by 120 minutes. Nucleotide supplementation had no distinct effect on lactate values in men or women. When sexes were compared, women demonstrated significantly lower lactate values at IP in both treatments. Lactate values are presented in FIG. 3.

Figure 4:
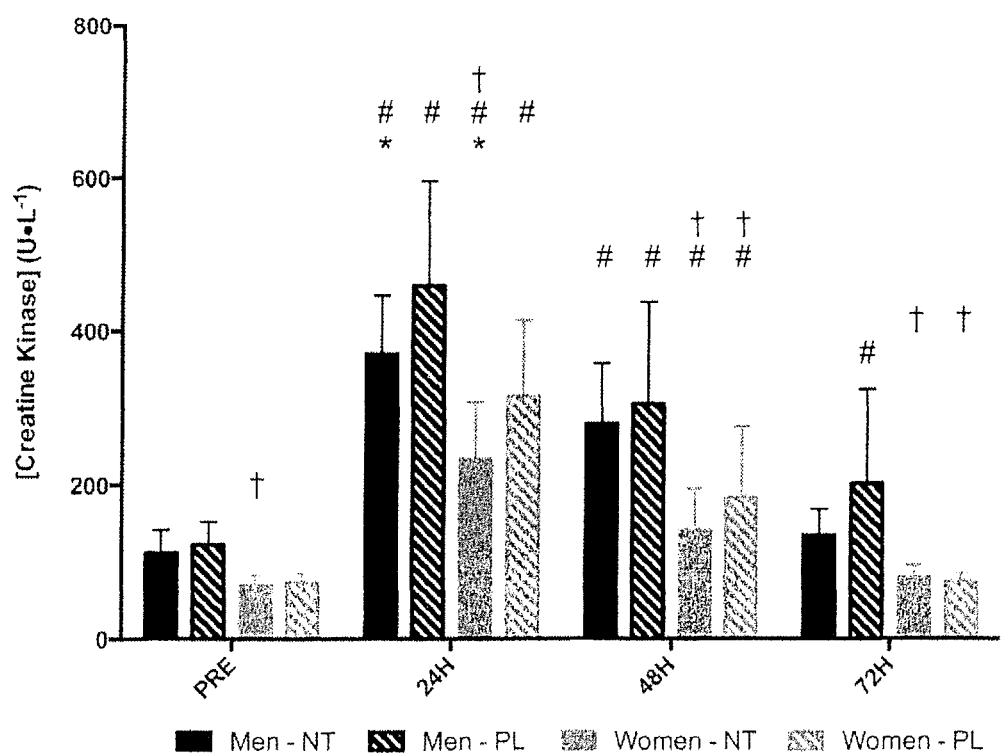
FIG. 4 illustrates the creatine kinase response to resistance exercise.
Figure 5:
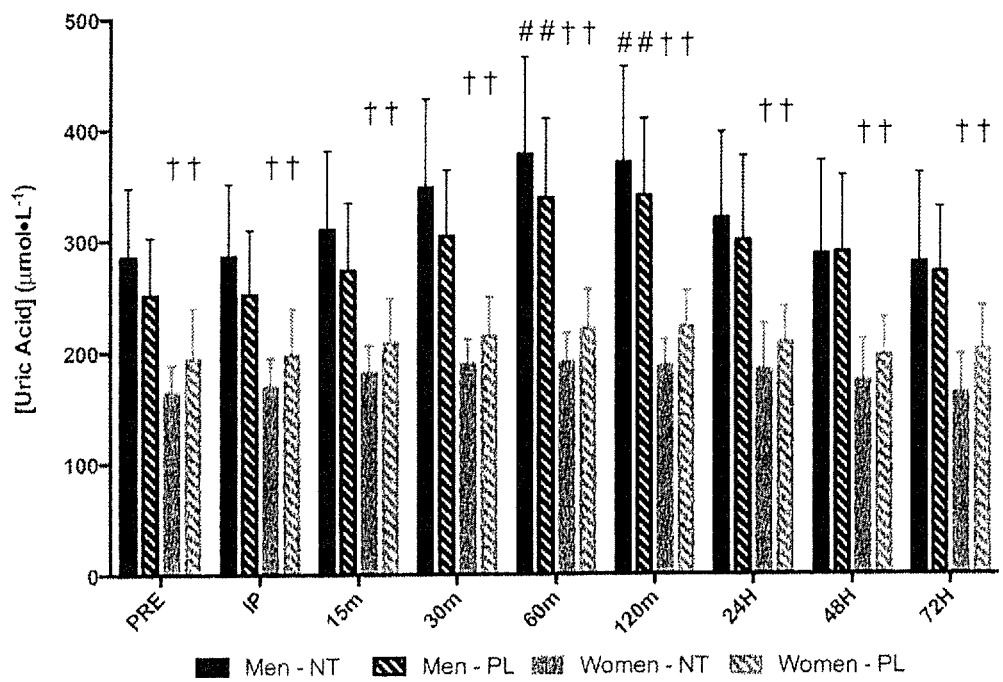
FIG. 5 illustrates the uric acid response to resistance exercise.

During the recovery period, CK values were significantly elevated above baseline values in men in women, regardless of the treatment condition. The CK values 24 hours after AHREP were significantly lower in nucleotide-supplemented groups than in the placebo treatment groups. Sex differences in CK were observed at baseline and recovery in the nucleotide-supplemented groups, but only during recovery in the placebo groups. The CK values are presented in FIG. 4. Significant uric acid increases were observed in men under both treatments at 60 and 120 minutes; however, no significant changes were observed in women. When compared with men, women demonstrated significantly lower uric acid values at all time points. No significant effects for nucleotide supplementation were observed in either sex. Uric acid values are presented in FIG. 5.

A similar post-AHREP increase in the neutrophil count was observed after both treatments in men and women. Lymphocytes also exhibited a significant time effect, in which all groups experienced elevated counts at IP, and a subsequent decrease below baseline within 30 minutes. Monocytes were elevated at IP regardless of treatment or sex. Men and women in the placebo treatment demonstrated a decrease in the monocytes below baseline values during the acute post-AHREP period, but this treatment effect was not statistically significant. Women exhibited significantly lower monocyte counts at IP in both treatments and at 48 hours post-AHREP in the placebo condition. The examined leukocyte populations did not seem to respond to nucleotide supplementation. Absolute leukocyte counts are shown in Tables 1 and 2.

TABLE 1

Average immune cell counts after nucleotide supplementation in men.*

| | Neutrophils | | Lymphocytes | | Monocytes | |
|---|---|---|---|---|---|---|
| Time | Nucleotide | Placebo | Nucleotide | Placebo | Nucleotide | Placebo |
| PRE | 3,057 ± 827 | 3,353 ± 1,674 | 2,033 ± 502 | 1,996 ± 624 | 458 ± 89 | 478 ± 126 |
| IP | 4,821 ± 1,339† | 5,548 ± 2,739† | 4,528 ± 1,246† | 4,108 ± 1,337† | 922 ± 209† | 1,001 ± 317† |
| 15 min | 4,134 ± 1,231† | 4,479 ± 1,991† | 2,918 ± 967† | 2,635 ± 1,040† | 585 ± 163 | 647 ± 225† |
| 30 min | 3,449 ± 1,112 | 3,898 ± 1,693† | 1,688 ± 553† | 1,540 ± 483† | 418 ± 92 | 451 ± 112 |
| 60 min | 3,457 ± 1,884 | 4,138 ± 1,990† | 1,253 ± 310† | 1,194 ± 303† | 384 ± 87 | 414 ± 106† |
| 120 min | 5,475 ± 2,988† | 5,512 ± 2,877† | 1,250 ± 259† | 1,261 ± 312† | 421 ± 81 | 494 ± 132 |
| 24 h | 3,337 ± 714 | 3,978 ± 2,158 | 1,739 ± 725 | 1,645 ± 550 | 472 ± 107 | 485 ± 144 |
| 48 h | 3,023 ± 459 | 3,497 ± 1,592 | 1,902 ± 588 | 1,813 ± 529 | 472 ± 107 | 545 ± 168 |
| 72 h | 3,328 ± 953 | 3,336 ± 1,792 | 1,929 ± 663 | 1,687 ± 363 | 527 ± 138 | 551 ± 132† |

*PRE = before acute heavy resistance exercise protocol; IP = immediately after acute heavy resistance exercise protocol.
†Significantly different from the corresponding PRE value ($p \leq 0.05$).

TABLE 2

Average immune cell counts after nucleotide supplementation in women.*

| | Neutrophils | | Lymphocytes | | Monocytes | |
|---|---|---|---|---|---|---|
| Time | Nucleotide | Placebo | Nucleotide | Placebo | Nucleotide | Placebo |
| PRE | 3,364 ± 1985 | 3,576 ± 2,681 | 2,337 ± 753 | 2,822 ± 961 | 482 ± 235 | 550 ± 473 |
| IP | 5,636 ± 3,631† | 4,626 ± 1,635† | 3,898 ± 828† | 3,887 ± 742† | 681 ± 256†‡ | 720 ± 195†‡ |
| 15 min | 4,417 ± 2,814† | 3,766 ± 1,771 | 2,063 ± 527† | 2,458 ± 330 | 491 ± 308 | 467 ± 194 |
| 30 min | 4,027 ± 2,485† | 3,485 ± 1932 | 1,498 ± 401† | 1,759 ± 349† | 362 ± 116 | 401 ± 170† |
| 60 min | 4,310 ± 2,431† | 4,348 ± 1,890† | 1,366 ± 348† | 1,640 ± 401† | 383 ± 208 | 399 ± 160† |
| 120 min | 5,440 ± 2,553† | 5,339 ± 1,905† | 1,454 ± 439† | 1,625 ± 340† | 440 ± 262 | 407 ± 174† |
| 24 h | 2,714 ± 1,044 | 3,333 ± 1,426 | 2,105 ± 594 | 2,351 ± 683 | 445 ± 297 | 443 ± 117 |
| 48 h | 3,210 ± 1,609 | 3,508 ± 1,343 | 2,122 ± 628 | 2,327 ± 554 | 476 ± 287 | 429 ± 134‡ |
| 72 h | 3,083 ± 1,882 | 3,134 ± 1,426 | 2,000 ± 525 | 2,270 ± 596 | 466 ± 344 | 442 ± 151 |

*PRE = before acute heavy resistance exercise protocol; IP = immediately after acute heavy resistance exercise protocol.
†Significantly different from the corresponding PRE value ($p \leq 0.05$).
‡Significantly different from the corresponding value in men.

Figure 6:
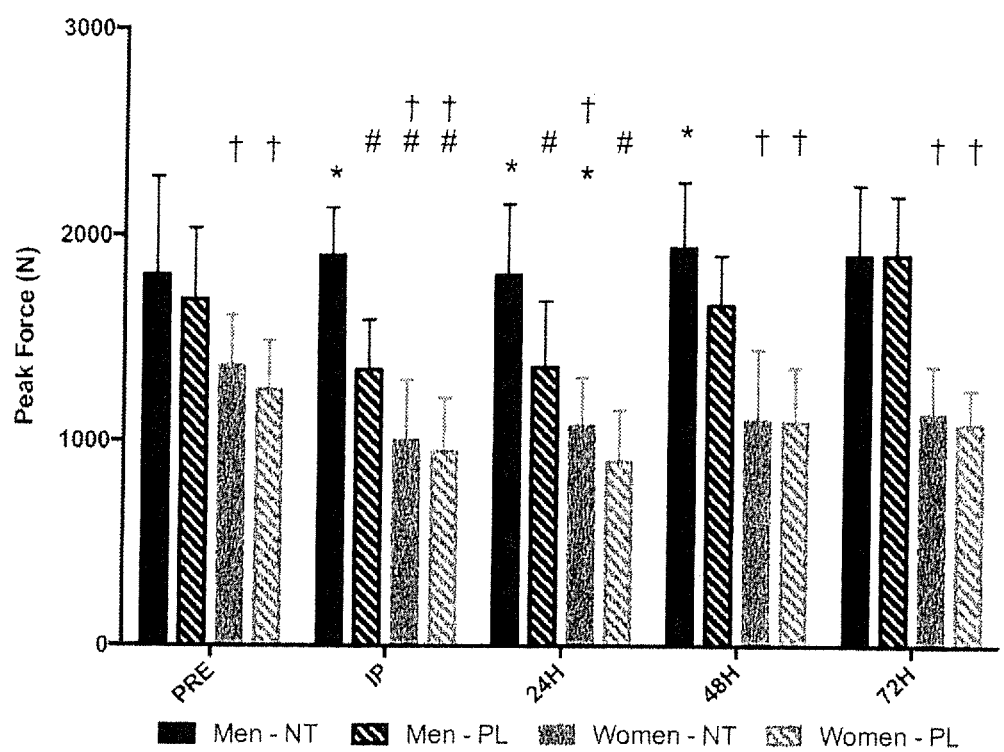
FIG. 6 illustrates the isometric force response to resistance exercise.

The AHREP had a significant detrimental effect on isometric force generation in men and women under placebo treatment. Isometric force generation returned to baseline values in nucleotide-supplemented women within 24 hours of the AHREP; however, men and women under placebo treatment required 48 hours for full recovery. Men receiving the nucleotide supplementation demonstrated no impairment of isometric force immediately after the protocol or during the recovery days. Compared with men, women demonstrated lower isometric force values at all time points for both treatments. Isometric force values are presented in FIG. 6.

Figure 7:
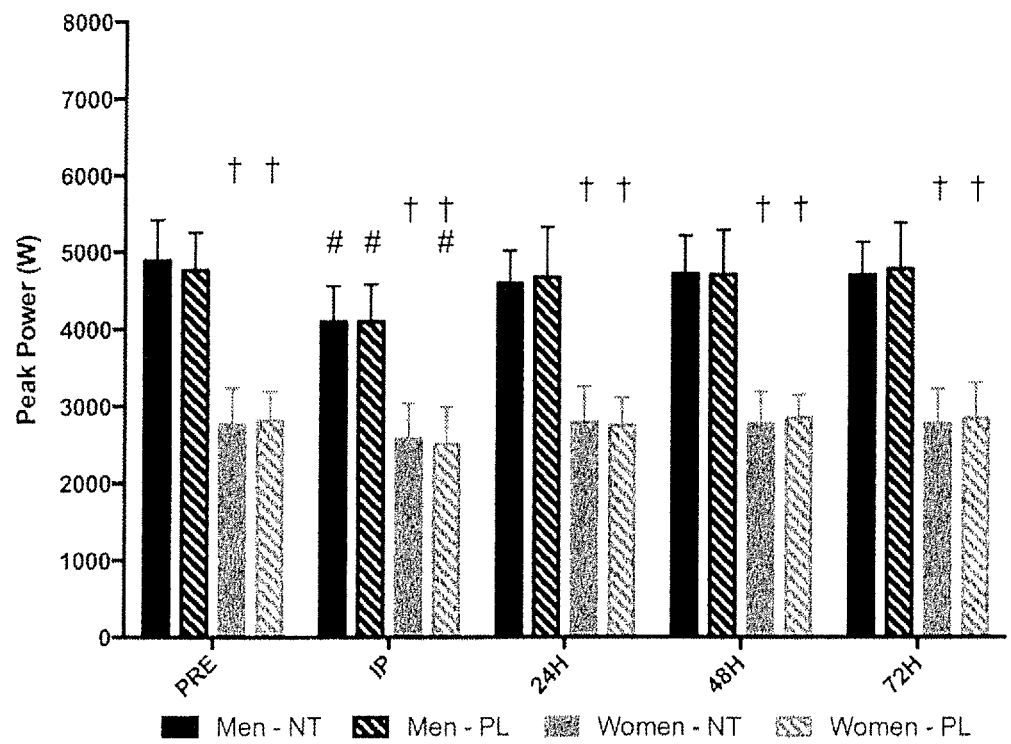
FIG. 7 illustrates the countermovement jump peak power response to resistance exercise.

Decrements in countermovement jump peak power were observed immediately after the AHREP in all subjects; however, values returned to baseline within 24 hours. No effects of nucleotide supplementation were observed. Similar to isometric force, women demonstrated lower peak power values at all times and treatments when compared with men. Countermovement jump peak power values are presented in FIG. 7.

Discussion

The primary finding of this investigation is that a dietary nucleotide supplement reduced markers of HPA and inflammatory activity, and these changes corresponded with reductions in tissue damage and the preservation of force production capabilities. Sex-specific differences in the response to nucleotide supplementation included the absence of improvement of physical recovery in women, who tended to demonstrate less inflammatory activity (lower MPO), and lower lactate, CK, and uric acid generally. These sexually dimorphic observations indicate that nucleotide supplementation produced modest positive effects primarily in men, who might have differed from women in terms of absolute exertion, normal or stress-related nucleotide metabolism, or immune/inflammatory responses to heavy resistance exercise.

Acute resistance exercise consistently results in transient increases in cortisol values. In accordance with previous findings, post-AHREP increases in cortisol were observed in both men and women with placebo. In contrast, significantly lower post-AHREP cortisol increases were observed in the male or female nucleotide groups.

The oxidative enzyme, MPO, is released from activated neutrophils and serves as an indirect measure of neutrophil activation and innate immune activity. MPO increased acutely after the AHREP. Although acute increases were observed in both placebo and nucleotide supplemented groups, MPO values were significantly lower after nucleotide supplementation. Additionally, decreased pre-AHREP MPO values were observed in women.

The AHREP induced significant muscle damage in all groups. Although elevated above baseline, CK values were significantly lower in the nucleotide-supplemented groups at the 24-hour post-AHREP time point. Reduced CK values 24 hours but not 48 or 72 hours after AHREP suggests that the nucleotide supplement reduced exercise-induced muscle damage, rather than improving recovery. Generally, because neutrophil activation is associated with the production of reactive oxygen species, which promote secondary (inflammation-induced) muscle damage, reductions in MPO may partially explain reductions in muscle damage.

In accordance with the attenuated cortisol response, neutrophil activation, and muscle damage, nucleotide supplementation attenuated performance decrements. After nucleotide supplementation, men produced greater isometric force immediately after the AHREP and 24 and 48 hours later. Women also demonstrated greater isometric force, but only 24 hours after exercise. As structural muscle damage can impair force generation, these observations are likely explained by reductions in muscle damage.

Regardless of sex or treatment, all leukocyte populations were affected by the AHREP. The lack of differences was surprising, given the differences in immune function, as well as previous investigations. These findings suggest the effects of nucleotide supplementation on immune cell activity are independent of changes in absolute leukocyte counts.

While various embodiments of the present invention have been described in detail, it is apparent that modifications and adaptations of those embodiments will occur to those skilled in the art. However, it is to be expressly understood that such modifications and adaptations are within the spirit and scope of the present invention.

What is claimed is:

1. A method to inhibit endurance exercise-induced production of cortisol, comprising administering a composition to an athlete engaging in endurance exercise, wherein the composition comprises yeast extract comprising dietary nucleotides, L-glutamine, L-methionine, L-lysine, riboflavin, folate, biotin, and pantothenic acid; and a carbohydrate component.

2. The method of claim 1, wherein the composition is administered prior to the exercise.

3. The method of claim 1, wherein the composition is administered prior to the exercise for at least 1 week.

4. The method of claim 1, wherein the composition is administered prior to the exercise for at least 2 weeks.

5. The method of claim 1, wherein the composition is administered after the exercise.

6. The method of claim 1, wherein the composition is administered after the exercise for at least 1 week.

7. The method of claim 1, wherein the composition is administered after the exercise for at least 2 weeks.

8. The method of claim 1, wherein the dietary nucleotides comprise RNA and DNA.

9. The method of claim 1, wherein the yeast extract is an extract of a yeast selected from the group consisting of *Saccharomyces cerevisiae* and *Candida utilis*.

10. The method of claim 1, wherein the dietary nucleotides are administered in an amount between 10 mg and 1000 mg on a daily basis, wherein the composition is administered prior to the exercise for at least 1 week.

11. The method of claim 1, wherein the dietary nucleotides are administered in an amount between 100 mg and 900 mg on a daily basis, wherein the composition is administered prior to the exercise for at least 1 week.

12. The method of claim 1, wherein the dietary nucleotides are administered in an amount between 400 mg and 800 mg on a daily basis, wherein the composition is administered prior to the exercise for at least 1 week.

13. The method of claim 1, wherein the endurance exercise is selected from the group consisting of long distance running, cycling, swimming, hiking, triathlon, softball, baseball, soccer, basketball, hockey, football, rugby, tennis, and lacrosse.

14. A method to inhibit endurance exercise-induced production of myeloperoxidase, comprising administering a composition to an athlete engaging in endurance exercise, wherein the composition comprises yeast extract comprising dietary nucleotides, L-glutamine, L-methionine, L-lysine, riboflavin, folate, biotin, and pantothenic acid; and a carbohydrate component.

* * * * *